United States Patent [19]

Seo et al.

[11] Patent Number: 5,391,558
[45] Date of Patent: Feb. 21, 1995

[54] COMPOSITION FOR ACCELERATING HEALING OF WOUND

[75] Inventors: Akira Seo, Wakayama; Kunikazu Hiraga, Osaka; Hiroyasu Koga, Osaka; Yoshimi Niwano, Osaka, all of Japan

[73] Assignee: Nihon Nohyaku Co., Ltd., Tokyo, Japan

[21] Appl. No.: 111,453

[22] Filed: Aug. 25, 1993

[51] Int. Cl.$^6$ .................. A61K 31/415; C07D 403/00
[52] U.S. Cl. ..................... 514/341; 514/359; 514/383; 548/255; 548/267.4; 548/311.1
[58] Field of Search ......... 514/341, 359, 383; 548/336, 255, 267.4

[56] References Cited

U.S. PATENT DOCUMENTS

| | | | |
|---|---|---|---|
| 4,206,119 | 6/1980 | Harrison et al. | 424/246 |
| 4,206,305 | 6/1980 | Harrison et al. | 424/246 |
| 4,636,519 | 1/1987 | Seo et al. | 514/397 |
| 4,738,976 | 4/1988 | Seo et al. | 514/341 |

FOREIGN PATENT DOCUMENTS

| | | | |
|---|---|---|---|
| 4-68308 | 11/1992 | Japan | 249/8 |
| 5271226 | 10/1993 | Japan. | |
| 2263234 | 7/1993 | United Kingdom. | |

OTHER PUBLICATIONS

Windholz et al, *The Merck Index*, p. 897, No. 5593 (1987).

*Primary Examiner*—Johann Richter
*Assistant Examiner*—Catherine S. Kilby Scalzo
*Attorney, Agent, or Firm*—Sughrue, Mion, Zinn, Macpeak & Seas

[57] ABSTRACT

A composition for accelerating healing of a wound is disclosed, comprising as an active ingredient a compound represented by formula (I):

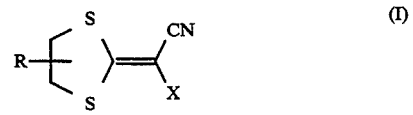

wherein R represents a hydrogen atom, a phenyl group or a phenyl group substituted with a halogen atom, a $C_1$–$C_6$ alkyl group, a hydroxyl group or a $C_1$–$C_6$ alkoxy group; and X represents a 1-imidazolyl group or a 1,2,4-triazol-1-yl group.

4 Claims, No Drawings

COMPOSITION FOR ACCELERATING HEALING OF WOUND

FIELD OF THE INVENTION

This invention relates to a composition for accelerating healing of a wound.

BACKGROUND OF THE INVENTION

A wound is a kind of injuries to the body ad includes incisions, wounds of gastrointestinal tracts, gastric ulcers, burns, detachment, lacerations, incision, pressure ulcers called decubitus or bed sore, erosion, and lesions of surface tissues due to infection. In particular, it is desirable to accelerate healing of a surgical wound by a positive and direct treatment without relying on spontaneous cure because a patient having undergone a surgical operation generally has considerably reduced physical strength. Further, bed sore not only causes pain to a patient but entails a heavy expenditure for healing, and is expected to give rise to a great social problem with the recent increase in aged population. Healing of these wounds generally depends on synthesis of connective tissues and epithelial tissues by cell proliferation. A drug which stimulates or accelerates the differentiation and proliferation of cells at the lesion is believed valuable in healing of a wound.

Known drugs for accelerating healing of a wound mainly include extracts of naturally occurring substances, e.g., aloe, antibiotics, antiphlogistics, kallikrein, adenine, nicotinic acid, allantoin, vitamin A, zinc, c-AMP derivatives (see JP-A-63-107935, the term "JP-A" as used herein means an "unexamined published Japanese patent application"), etc., and improved formulations for improving absorbability of the active ingredient have been proposed. With the recent various dermatohistological elucidations, an attempt at applying an epidermal growth factor (EGF) to postoperative healing of a wound has also been reported (see JP-A-3-106823).

However, the known compounds exemplified above have not been considered to have sufficient effects on healing a wound. Accordingly, it has been demanded to find a drug which directly acts on the develop to heal a wound.

SUMMARY OF THE INVENTION

Under the above-mentioned circumstances, the present inventors have extensively conducted investigations for the purpose of providing a drug for topical use effective for healing of a skin wound. As a result, they have found an excellent effect in a compound represented by formula (I) shown below and completed the present invention.

The present invention provides a composition for accelerating healing of a wound comprising as an active ingredient a compound represented by formula (I):

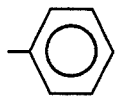

wherein R represents a hydrogen atom, a phenyl group or a phenyl group substituted with a halogen atom, a $C_1$–$C_6$ alkyl group, a hydroxyl group or a $C_1$–$C_6$ alkoxy group; and X represents a 1-imidazolyl group or a 1,2,4-triazol-1-yl group.

Although many of the compounds represented by formula (I) are known to exhibit antifungal (see U.S. Pat. No. 4,636,519, U.S. Pat. No. 4,738,976 and JP-B-4-68308) and antimicotic activities (see U.S. Pat. No. 4,636,519 and U.S. Pat. No. 4,738,976), it is unknown that the compounds of formula (I) possess an action of accelerating healing of a skin wound.

DETAILED DESCRIPTION OF THE INVENTION

While the compounds of formula (I) each embrace two geometrical isomers as illustrated below, the compounds may be used in the present invention either as one of the isomers or as an isomerical mixture.

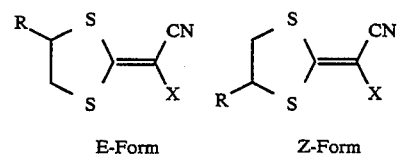

E-Form          Z-Form

Specific examples of the compounds which can be used in the present invention are shown in Tables 1 and 2 below for illustrative purposes only but not for limitation. Physicochemical properties of these compounds are also shown. In the Tables, "mp" is a melting point, "$n_D$" is a refractive index, and the δ values (ppm) in NMR spectra are those measured in $CDCl_3$ using TMS as a standard.

TABLE 1

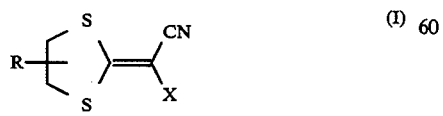
(Ia)

| Compound No. | R | Physicochemical Properties |
|---|---|---|
| 1 | H | mp: 125.6° C. |
| 2 | 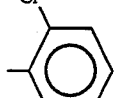 | mp: 111–112° C. (E-form) |
| 3 | 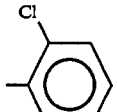 | mp: 119.4° C. (Z-form) |
| 4 | 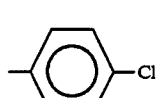 | mp: 141.5° C. (E-form) |
| 5 | 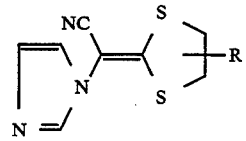 | $n_D^{24}$: 1.6083 |

TABLE 1-continued (Ia)

[Structure: azole-N-C(NC)=C(S-CHR-S) ring system with R substituent]

| Compound No. | R | Physicochemical Properties |
|---|---|---|
| 6 | 2-Br-phenyl | viscous oily substance (Z-form) NMR δ: 3.54–4.20(m, 2H), 5.69 (dd, 1H), 7.00–7.75(m, 7H) |
| 7 | 2-Br-phenyl | viscous oily substance (E-form) NMR δ: 3.45–4.10(m, 2H), 5.76 (dd, 1H), 7.00–7.85(m, 7H) |
| 8 | 4-Br-phenyl | viscous oily substance (Z-form) NMR δ: 3.6–4.0(m, 2H), 5.22 (dd, 1H), 6.9–7.81(m, 7H) |
| 9 | 4-Br-phenyl | mp: 148.8° C. (E-form) |
| 10 | 2-F-phenyl | viscous oily substance (Z-form) |
| 11 | 2-F-phenyl | mp: 119° C. (E-form) |
| 12 | 4-F-phenyl | viscous oily substance NMR δ: 3.6–3.9(m, 2H), 5.1–5.5(m, 1H), 6.9–7.8(m, 7H) |
| 13 | 2-CH$_3$-phenyl | $n_D^{13}$: 1.6313 (Z-form) |
| 14 | 2-CH$_3$-phenyl | mp: 123.3° C. (E-form) |
| 15 | 4-CH$_3$-phenyl | $n_D^{24}$: 1.6360 |

TABLE 1-continued (Ia)

[Structure: azole-N-C(NC)=C(S-CHR-S) ring system with R substituent]

| Compound No. | R | Physicochemical Properties |
|---|---|---|
| 16 | 2-i-C$_3$H$_7$-phenyl | $n_D^{16}$: 1.6196 |
| 17 | 2-CH$_3$O-phenyl | viscous oily substance (Z-form) |
| 18 | 2-CH$_3$O-phenyl | viscous oily substance (E-form) NMR δ: 3.71(d, 2H), 3.82(s, 3H), 5.68(t, 1H), 6.87, 7.00 and 6.72 (each 1H, H of azole ring), 7.00–7.60(m, 4H) |
| 19 | 4-OCH$_3$-phenyl | viscous oily substance (Z-form) NMR δ: 3.75(d, 2H), 3.77(s, 3H), 5.17(t, 1H), 6.74–7.60(m, 7H) |
| 20 | 4-OCH$_3$-phenyl | viscous oily substance (E-form) NMR δ: 3.67(d, 2H), 3.80(s, 3H), 5.24(t, 1H), 6.70–7.65(m, 7H) |
| 21 | 4-OH-phenyl | mp: 219–221° C. (E-form) |

TABLE 2

(Ib)

[Structure: triazole-N-C(NC)=C(S-CHR-S) ring system with R substituent]

| Compound No. | R | Physicochemical Properties |
|---|---|---|
| 22 | H | mp: 102.6° C. |
| 23 | phenyl | viscous oily substance |
| 24 | 3-Cl-phenyl | mp: 71–73° C. (E-form) |

TABLE 2-continued (Ib) structure: imidazole-N with NC, connected via C=C to 1,3-dithiolane bearing R

| Compound No. | R | Physicochemical Properties |
|---|---|---|
| 25 | o-chlorophenyl | mp: 75–77° C. (Z-form) |
| 26 | o-bromophenyl | $n_D^{19}$: 1.6558 |
| 27 | p-chlorophenyl | viscous oily substance NMR δ: 3.82(d, 2H), 5.31(t, 1H), 7.18–7.51(m, 4H), 8.11(s, 1H), 8.39(s, 1H) |
| 28 | p-bromophenyl | viscous oily substance |
| 29 | p-fluorophenyl | $n_D^{20.5}$: 1.6232 |
| 30 | o-tolyl | mp: 115.0° C. |
| 31 | p-tolyl | $n_D^{24}$: 1.6162 |
| 32 | o-isopropylphenyl | viscous oily substance |
| 33 | p-methoxyphenyl | viscous oily substance |
| 34 | p-hydroxyphenyl | mp: 214–216° C. (E-form) |

R is preferably o-chlorophenyl, p-hydroxyphenyl or p-tolyl group.

Of the compounds represented by formula (I), those represented by formula (I'):

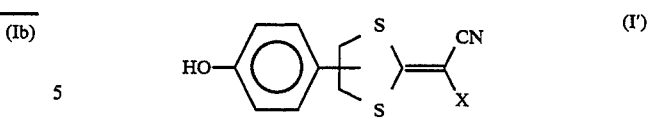

wherein X is as defined above, are novel compounds.

The compound of the present invention can be converted to the salt by techniques known in the art. Examples of such salts include hydrochlorides, sulfates and nitrate.

The composition for accelerating healing of a wound according to the present invention can be prepared as various formulations such as solutions, emulsions, ointments, creams, lotions, poultices, tablets, granules, capsules, ampuls, etc. by compounding with pharmaceutically acceptable carriers. Specific examples of the pharmaceutically acceptable carriers are polyethylene glycol, 1,2-propanediol, glycerole stearate, spermaceti, isopropyl myristate, polysolvate, stearyl alcohol, cetanol, sorbitan monostearate, methyl p-hydroxybenzoate, propyl p-hydroxybenzoate, dibutylhydroxytoluene, calcium hydrogenphosphate, lactose, starch, heavy magnesium oxide, water, glucose solution and polyvinyl alcohol.

The compound of formula (I) is usually mixed with a base in an amount usually of from 0.01 to 50% by weight, preferably from 0.05 to 10% by weight, and more preferably from 0.1 to 3% by weight, based on the base weight.

The preparations of the present invention can be given orally or parenterally. When the preparations are orally given to adult patients, it is desirable that the patients are dosed with 1 to 100 mg/kg of body weight.

The present invention will now be illustrated in greater detail with reference to Formulation Examples and Test Examples, but it should be understood that the present invention is not to be construed as being limited thereto. All the parts and percents are by weight unless otherwise indicated.

Synthesis Example for the compounds represented by formula (I) is described below. The other compounds are able to prepare according to the similar method described in U.S. Pat. No. 4,636,519.

SYNTHESIS EXAMPLE

Synthesis of 2-(1-Imidazolyl)-2-{4-(hydroxyphenyl)-1,3-dithiolane-2-ylidene}acetonitrile (Compound 21).

In 40 ml of dimethyl sulfoxide were dissolved 4.6 g (0.004 mol) of 1-cyanomethylimidazole, 3.1 g (0.005 mol) of carbon disulfide and 5.2 g of pottassium hydroxide powder by stirring at room temperature for 1 hour to prepare a dithiolate solution. The solution was added dropwise to a solution of 14.8 g (0.04 mol) of 1,2-dibromo-1-(4-t-butoxyphenyl)ethane in 40 ml of dimethyl sulfoxide at 30° C., followed by stirring for 2 hours. To the reaction mixture was added 200 ml of icewater, and the mixture was extracted with ethyl acetate. The organic layer was washed with water, dried over magnesium sulfate, and concentrated to obtain a mixture of geometric isomers as a viscous oily substance. Purification of the product by silica gel chromatography gave 2.4 g (yield: 16.8%) of a Z-isomer and 4.5 g (yield: 31.5%) of an E-isomer both as a viscous oily substance.

The resulting E-isomer was dissolved in 10 ml of trifluoroacetic acid, and the solution was stirred at room temperature for 1 hour. The reaction mixture was concentrated under reduced pressure, and the residue was dissolved in ethyl acetate and washed with an aqueous sodium hydrogencarbonate. The organic layer was dried over magnesium sulfate, and the solvent was removed by distillation under reduced pressure. Recrystallization of the residue from ethanol yielded 2.4 g (66.5%) of the titled compound (mp: 219°–221° C.).

FORMULATION EXAMPLE 1

| | |
|---|---|
| Compound of the invention | 1 part |
| Polyethylene glycol 400 | 99 parts |

The above components were mixed to dissolve the active ingredient to prepare a solution for topical application.

FORMULATION EXAMPLE 2

| | |
|---|---|
| Compound of the invention | 2 parts |
| Polyethylene glycol 400 | 49 parts |
| Polyethylene glycol 4000 | 49 parts |

The above components were mixed while heating to dissolve the active ingredient and cooled to prepare an ointment.

FORMULATION EXAMPLE 3

| | |
|---|---|
| Compound of the invention | 3 parts |
| 1,2-Propanediol | 5 parts |
| Glycerol stearate | 5 parts |
| Spermaceti | 5 parts |
| Isopropyl myristate | 10 parts |
| Polysolvate | 4 parts |

A mixture of the above components was warmed and cooled, and 68 parts of water were added thereto while stirring to prepare a cream.

FORMULATION EXAMPLE 4

| | |
|---|---|
| Compound of the invention | 0.1 part |
| Stearyl alcohol | 5.0 parts |
| Cetanol | 5.0 parts |
| Middle-chain fatty acid triglyceride | 10.0 parts |
| Isopropyl myristate | 5.0 parts |
| Polysolvate 60 | 4.0 parts |
| Sorbitan monostearate | 1.0 part |
| Methyl p-hydroxybenzoate | 0.14 part |
| Propyl p-hydroxybenzoate | 0.06 part |
| Dibutylhydroxytoluene | 0.02 part |
| Purified water | the balance |

The above components were mixed in a usual manner to prepare a cream.

FORMULATION EXAMPLE 5

| | |
|---|---|
| Compound of the invention | 50 parts |
| Starch | 10 parts |
| Lactose | 15 parts |
| Crystalline cellulose | 20 parts |
| Polyvinyl alcohol | 5 parts |
| Water | 30 parts |

The above-mentioned components were homogenously kneaded, granulated, dried and sieved to obtain granules.

TEST EXAMPLE 1

Animals were shaved on their back, and two circular excisional wounds (1 cm diameter) per animal were made by cutting out the full-thickness skin with scissors. From the next day of the wounding, a cream containing 0.5% or 1% of Compound No. 4 which prepared in accordance with Formulation Example 4 was topically applied daily to the wounded site in the amount of 60 mg/site/day everyday. For comparison, a commercially available 5% Solcoseryl ointment (produced by Tobishi pharmaceutical Co., Ltd.) was applied in the same amount. The wound area was treated on the 4th, 6th, and 8th days of application, and the square measure was calculated by an Image analyzer (SPICCA-II, manufactured by Olympus Co., Ltd.). Date is expressed as % of the initial wound area which was obtained on the next day of wounding. On the 5th, 7th or 9th day of application, two rats per group were sacrificed, and the involved skin was excised for light microscopic observation.

The results of measurement of the wound area are shown in Table 3 below. Each area ratio based on the initial wound area as 100%. Because two of the animals of each group were put to death for histopathological examinations on the 5th, 7th and 9th days of application, the number of involved sites under observation reduced by two on each killing.

TABLE 3

| Test Group | Area Ratio of Wound (%) | | |
|---|---|---|---|
| | 4th Day | 6th Day | 8th Day |
| Untreated group | 87 | 74 | 41 |
| Control group (treated with the base alone) | 99 | 70 | 40 |
| 5.0% Solcoseryl group | 87 | 35 | 11 |
| 0.5% Compound 4 group | 75 | 40 | 9 |
| 1.0% Compound 4 group | 77 | 39 | 11 |

As is apparent from Table 3, the compound of the present invention shows a higher or equal activity of accelerating healing of a wound than or to Solcoseryl used as a reference drug. Histopathological examinations also revealed the activity of the compound in acceleration of angiogensis, elogenation and differentitation of the epidermis, and formation of granulation tissue in the dermis which are important for the healing process of a wound.

TEST EXAMPLE 2

Rats were wounded on their back in the same manner as in Test Example 1. From the next day, a 1% polyethylene glycol 400 (PEG 400) solution of a test compound was applied daily in a volume of 0.1 ml/site/day, and the area ratio of the wound based on the initial wound was measured on the 5th and 7th day of application. The results obtained are shown in Tables 4 and 5 below.

TABLE 4

| Test Group | Area Ratio of Lesion (%) | |
|---|---|---|
| | 5th Day | 7th Day |
| Untreated group | 69 | 47 |
| Control group (treated with only PEG 400) | 62 | 34 |
| Compound No. 1 | 67 | 25 |

TABLE 4-continued

| Test Group | Area Ratio of Lesion (%) | |
| --- | --- | --- |
| | 5th Day | 7th Day |
| Compound No. 2 | 63 | 25 |
| Compound No. 3 | 52 | 20 |
| Compound No. 4 | 51 | 21 |
| Compound No. 22 | 62 | 25 |
| Compound No. 24 | 65 | 29 |

TABLE 5

| Test Group | Area Ratio of Lesion (%) | |
| --- | --- | --- |
| | 5th Day | 7th Day |
| Untreated group | 61 | 36 |
| PEG 400 group | 57 | 31 |
| Compound No. 4 | 37 | 22 |
| Compound No. 15 | 43 | 21 |
| Compound No. 20 | 47 | 28 |
| Compound No. 21 | 33 | 15 |
| Compound No. 24 | 39 | 25 |

As shown in Tables 4 and 5, the compounds according to the present invention as well as Compound No. 4 possess a wound healing accelerating activity.

TEST EXAMPLE 3

Cotton pellets weighing 39–41 mg were sterilized by autoclaving, immersed with ethanol solution of Compound No. 4 (0.2 ml/pellet), and dried under negative pressure. Under light ether anesthesia, two pellets were subcutaneously implanted under bilateral Scapla of rats, respectively, through dorsal skin incision. Each animal (each group containing 10 rats) was intramusculary injected a 1:1 mixture of penicillin G ($1 \times 10^4$ units/ml) and streptmycin (8 mg/ml) in a volume of 0.2 ml to prevent it from suffering from bacterial infection. Animals were sacrificed 7 days after implantation of pellets, and each granulation tissue including the pellet was excised to measure its dry weight. The results are shown in Table 6.

TABLE 6

| Test Group | Dry weight of granulation tissue including cotton pellet (mg) |
| --- | --- |
| Untreated group | 102.1 ± 5.2 |
| Control group (treated with the base only) | 93.0 ± 4.7 |
| 0.5 mg/pellet Compound No. 4 | 108.7 ± 10.4 |
| 1.0 mg/pellet Compound No. 4 | 123.7 ± 7.1 |
| 2.0 mg/pellet Compound No. 4 | 136.4 ± 14.1 |
| 4.0 mg/pellet Compound No. 4 | 130.6 ± 6.0 |

As shown in Table 6, Compound No. 4 increased the dry weight of granulation tissue by the cotton pellet implantation to show an activity of accelerating the formation of granulation tissue. The increases by the treatment with Compound No. 4 at dose more than 1 mg/pellet were significantly greater than those in controls.

As described above, a wound of the skin, etc. can be healed rapidly by applying the compound of the present invention as a composition for accelerating healing of the wound.

While the invention has been described in detail and with reference to specific examples thereof, it will be apparent to one skilled in the art that various changes and modifications can be made therein without departing from the spirit and scope thereof.

What is claimed is:

1. A topical composition for accelerating healing of a wound comprising as an active ingredient a compound represented by the formula (I'):

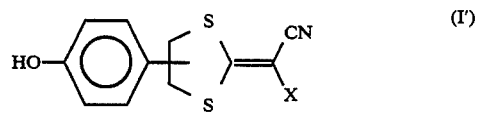

wherein X represents a 1-imidazolyl group or a 1,2,4-triazol-1-yl group.

2. A method for accelerating healing of a wound which comprises topically administering to a patient in need of such acceleration, a topical composition for accelerating healing of wound comprising, as an active ingredient, a compound represented by formula (I):

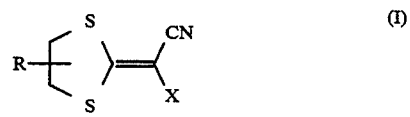

wherein R represents a hydrogen atom, a phenyl group or a substituted phenyl group, wherein the substituent on said substituted phenyl group is a halogen atom, a $C_1$–$C_6$ alkyl group, a hydroxyl group or a $C_1$–$C_6$ alkoxy group; and X represents a 1-imidazolyl group or a 1-triazolyl group; and a pharmaceutically acceptable carrier.

3. A topical composition for accelerating healing of a wound comprising, as an active ingredient, a compound represented by formula (I):

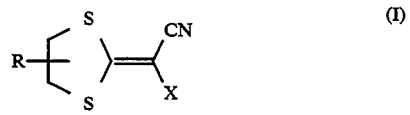

wherein R is a p-hydroxyphenyl group; and X represents a 1-imidazolyl group or a 1-triazolyl group; and a pharmaceutically acceptable carrier.

4. A method for accelerating healing of a wound which comprises topically administering to a patient in need of such acceleration the topical composition of claim 3.

* * * * *